(12) United States Patent
Carman et al.

(10) Patent No.: US 6,955,786 B2
(45) Date of Patent: *Oct. 18, 2005

(54) GASEOUS BLEND OF $CO_2$ AND $O_X$ AND ITS USE FOR BIOLOGICAL BURDEN REDUCTION

(75) Inventors: Gary B. Carman, Reno, NV (US); Steven K. Wirtz, Sparks, NV (US)

(73) Assignee: Cosmed Group, Inc., Jamestown, RI (US)

( * ) Notice: Subject to any disclaimer, the term of this patent is extended or adjusted under 35 U.S.C. 154(b) by 572 days.

This patent is subject to a terminal disclaimer.

(21) Appl. No.: 10/098,929

(22) Filed: Mar. 15, 2002

(65) Prior Publication Data

US 2002/0182104 A1 Dec. 5, 2002

Related U.S. Application Data

(63) Continuation-in-part of application No. 09/903,685, filed on Jul. 13, 2001, now Pat. No. 6,793,884, which is a continuation of application No. 09/217,581, filed on Dec. 22, 1998, now Pat. No. 6,284,193.
(60) Provisional application No. 60/276,041, filed on Mar. 16, 2001, and provisional application No. 60/068,668, filed on Dec. 23, 1997.

(51) Int. Cl.[7] ................................................. A61L 9/00
(52) U.S. Cl. ............................ 422/33; 422/22; 422/23; 422/28; 422/32; 422/186.07
(58) Field of Search ............................. 422/33, 22, 23, 422/28, 29, 30, 186.07, 292, 32

(56) References Cited

U.S. PATENT DOCUMENTS

| | | |
|---|---|---|
| 4,182,663 A | 1/1980 | Vaseen |
| 4,200,656 A | 4/1980 | Cohen et al. |
| 4,549,477 A | 10/1985 | McCabe, Jr. |
| 4,640,782 A | 2/1987 | Burleson |
| 4,889,708 A | 12/1989 | Latif et al. |
| 4,988,484 A | 1/1991 | Karlson |
| 4,989,363 A | 2/1991 | Doernemann |
| 4,998,377 A | 3/1991 | Tsutsumi et al. |
| 5,011,699 A | 4/1991 | Mitsuda et al. |
| 5,069,880 A | 12/1991 | Karlson |
| 5,120,512 A | 6/1992 | Masuda |
| 5,135,721 A | 8/1992 | Richard |
| 5,178,896 A | 1/1993 | Langner |

(Continued)

FOREIGN PATENT DOCUMENTS

| | | |
|---|---|---|
| DE | 34 15 301 A1 | 10/1985 |
| DE | 39 17 250 A1 | 5/1989 |
| JP | 02076562 A | 3/1990 |

OTHER PUBLICATIONS

European Patent Office, European Office Action dated May 26, 2003 in European Application No. 98 964 716.9–2113.
M. Margaret Barth et al, Ozone Storage Effects on Anthocyanin Content and Fungal Growth in Blackberries, Journal of Food Science, vol. 60, No. 6, pp. 1286–1288, (1995).
J. Kuprianoff, The Use of Ozone for the Cold Storage of Fruit Z. Kaltentechnik, 10:1–4 (1953) (in German with English Translation of major points) (Abstract).
Jae–Kun Chun, Yung–Jin Lee, Kyung–Man Kim, HongWon Lee, and Eu–Yung Jang, College of Agriculture & Life Science, Seoul National University, Korea), Sterilizing and Deodorizing Effect of UV–Ray Air Cleaner for Refrigerator; Korean J. Food Sci. Technol. 25(2): 174–177 (1993) (in Korean, English ABSTRACT).

*Primary Examiner*—Krisanne Jastrzab
(74) *Attorney, Agent, or Firm*—Patton Boggs LLP

(57) ABSTRACT

A gaseous blend of $CO_2$ and $O_x$ and a method for applying a continuous stream of a gaseous blend of $CO_2$ and $O_x$ to a material are disclosed. The gaseous blend and the method significantly reduce the biological load on consumer products, such as food products, botanicals and cosmetic ingredients; in building structures; on transportation containers; and in soil.

14 Claims, 2 Drawing Sheets

U.S. PATENT DOCUMENTS

| | | |
|---|---|---|
| 5,200,158 A | 4/1993 | Jacob |
| 5,241,803 A | 9/1993 | Griffin |
| 5,403,597 A | 4/1995 | Mueller |
| 5,413,758 A | 5/1995 | Caputo et al. |
| 5,464,457 A | 11/1995 | Winston et al. |
| 5,518,698 A | 5/1996 | Karlson et al. |
| 5,566,627 A | 10/1996 | Pryor |
| 5,624,635 A | 4/1997 | Pryor |
| 5,678,352 A | 10/1997 | Leitner et al. |
| 5,897,841 A | 4/1999 | Shroff |
| 6,027,667 A | 2/2000 | Horn Feja et al. |
| 6,066,348 A | 5/2000 | Yuan et al. |
| 6,197,081 B1 | 3/2001 | Schmidt |
| 6,284,193 B1 * | 9/2001 | Carman et al. ............... 422/33 |
| 6,793,884 B1 * | 9/2004 | Carman et al. ............... 422/33 |

* cited by examiner

GASEOUS BLEND OF CO₂ AND O$_X$ AND ITS USE FOR BIOLOGICAL BURDEN REDUCTION

CROSS-REFERENCE TO RELATED APPLICATIONS

This application continuation-in-part to U.S. application Ser. No. 09/903,685, filed Jul. 13, 2001 now U.S. Pat. No. 6,793,884, which is a continuation of application Ser. No. 09/217,581, filed Dec. 22, 1998 (now U.S. Pat. No. 6,284,193), which claims priority to provisional application Ser. No. 60/068,668, filed Dec. 23, 1997; and to provisional application Ser. No. 60/276,041, filed Mar. 16, 2001.

BACKGROUND OF THE INVENTION

1. Field of the Invention

The present invention generally relates to a gaseous blend of $CO_2$ and $O_X$ and a method for applying the gaseous blend that can be utilized to significantly reduce the biological load on consumer products such as food products, botanicals and cosmetic ingredients, which have traditionally been treated with commercial sterilants or fumigants such as ethylene oxide, propylene oxide, methyl bromide, hydrogen phosphide, phosphine, steam (heat), irradiation, and the like. The gaseous blend of $CO_2$ and $O_x$ and method for applying the gaseous blend can also be used to reduce biological load in enclosed structures and on transportation containers (e.g., wooden pallets and crates), which are often used to store food products, as well as to reduce biological load on other commodities, and, in particular, on soil.

2. Background of the Technology

Damage to food products, building structures and other commodities by insects and other pests accounts for billions of dollars of losses in the United States annually. Traditionally, a number of fumigants have been utilized to control these pests by their application under air tight tarpaulins, in sealed rooms and in steel chambers. The most widely used fumigants are methyl bromide, hydrogen phosphide and hydrogen cyanide. As disclosed in U.S. Pat. Nos. 6,284,193 and 6,334,979, many of these compounds pose hazardous conditions for application personnel and can form deleterious residues on the foodstuffs, building structures, transportation containers and commodities that are treated. Furthermore, some of the traditional fumigants have been identified with the formation of carcinogens and mutagens, thereby limiting the products that can be treated. All three of the primary employed gaseous fumigants; i.e., methyl bromide, hydrogen phosphide and hydrogen cyanide, have faced major regulatory restrictions and/or total phase out agreements. With these limitations in mind, the search for effective alternatives has led to the use of materials such as methyl iodide and sulfonyl fluoride. Unfortunately, these alternatives have limitations because of factors such as worker exposure, halogen content and damage to certain commodities.

Ozone ($O_3$) and its primary active component, atomic oxygen, have been used in water and commodity sterilization for about 100 years. Carbon dioxide ($CO_2$) has been used in conjunction with various pesticides to enhance their effectiveness by increasing the target organism's rate of respiration. As discussed in more detail below, however, prior treatment methods using $O_3$ or $CO_2$ have proven ineffective for many applications.

U.S. Pat. Nos. 5,624,635 and 5,566,627 disclose a method and apparatus for use of $O_3$ to treat soil.

U.S. Pat. Nos. 4,889,708; 5,403,597; 5,897,841 and 6,027,667 disclose the use of $CO_2$ as a carrier gas for phosphine fumigant.

U.S. Pat. No. 4,200,656 discloses the use of $CO_2$ as a carrier for methyl bromide in fumigation.

U.S. Pat. No. 4,998,377 discloses the use of $CO_2$ as a carrier for methyl bromide and hydrogen phosphide in fumigation.

U.S. Pat. No. 5,678,352 discloses the use of $CO_2$ as a carrier for toxic agents such as methyl bromide during fumigation.

U.S. Pat. No. 5,464,457 discloses the use of an ammonium carbonate ingredient that decomposes to ammonia and $CO_2$ in order to fumigate a plot of soil.

U.S. Pat. No. 4,989,363 discloses application of $CO_2$ in pesticidal quantities for fumigation. The process disclosed in U.S. Pat. No. 4,989,363 requires administration of $CO_2$ for a period of time of at least about 5 days.

U.S. Pat. No. 5,011,699 discloses the use of $O_3$ and $CO_2$ in specified ratios, i.e., from 1:2 to 2:1, to sterilize foodstuffs at reduced temperatures.

U.S. Pat. No. 6,066,348 discloses the use of $O_3$ and $CO_2$ at reduced temperature to disinfect a foodstuff.

Japanese Patent Publication No. 02076562A (Abstract) discloses the use of $O_3$, $CO_2$ and N gas to sterilize foodstuffs.

U.S. Pat. Nos. 6,283,193 and 6,334,979 disclose methods that use a gaseous mixture of oxygen-containing gases, i.e., $O_3$, $O_2$ and $O_1$, hereinafter referred to as $O_x$, in a vacuum chamber to reduce biological loads on foodstuffs and other commodities. Although such use of $O_x$ has proven successful in controlling insects and microbiological concerns for selected fruits, vegetables and other botanicals, because of phyto-toxic issues and the fact that $O_3$ readily converts to oxygen when exposed to an oxygen-rich atmosphere, there remains a need to treat foodstuffs and other commodities that cannot withstand treatment under vacuum.

The present inventors have surprisingly discovered that regardless of whether a vacuum is employed, for a number of commodities, a gaseous blend of $CO_2$ and $O_x$ having a specified ratio, i.e., about 90–99% $CO_2$ and about 1–10% $O_x$, preferably about 98–99% $CO_2$ and about 1–2% $O_x$, is highly effective in biological burden reduction. This surprising discovery permits the application of gaseous $O_x$ to products in many environments.

SUMMARY OF THE INVENTION

It is desirable to treat a wide variety of materials in a cost effective manner. The gaseous blend of $CO_2$ and $O_x$ and the method for applying the gaseous blend of the present invention permit fumigation (hereinafter referred to as "biological burden reduction") of a commodity on-site where the commodity is normally stored, thereby eliminating the need to transfer the commodity to another location for treatment.

The method of the present invention utilizes the gaseous blend of $CO_2$ and $O_x$ in a technologically advanced treatment system that overcomes limitations formerly encountered with $CO_2$ and/or $O_3$ treatment on biological burden. Most importantly, the method of the present invention eliminates the need for complex systems often employed in prior art methods. The method may be employed on-site, thereby eliminating the need to transfer material to a special processing location.

Accordingly, it is an object of the present invention to provide a gaseous blend of $CO_2$ and $O_x$ and a method for applying the gaseous blend of $CO_2$ and $O_x$ to reduce biological burden from food products and other commodities, building structures, transportation containers and soil.

It is another object of the present invention to provide a gaseous blend of $CO_2$ and $O_x$ and method for applying the gaseous blend of $CO_2$ and $O_x$ to reduce biological burden from food products and other commodities, building structures, transportation containers and soil in a safe manner.

It is, therefore, an object of the present invention to eliminate the health risks that are associated with the reduction of biological burden from food products and other commodities, building structures, transportation containers and soil.

It is a further object of the present invention to provide a simple, efficient and economical gaseous blend of $CO_2$ and $O_x$ and a method for applying the gaseous blend of $CO_2$ and $O_x$ for reducing biological burden from food products and other commodities, building structures, transportation containers and soil that can be used on-site.

In accordance with the above and other objects, the inventive gaseous blend consists of about 90–99%, preferably about 98–99%, $CO_2$ and about 1–10%, preferably about 1–2%, $O_x$. The inventive method for applying the gaseous blend comprises applying a continuous stream of $CO_2$ and $O_x$ gas to a material. Preferably, the gaseous blend is applied at an elevated temperature, e.g., approximately 45° F. to 140° F., and more preferably at about 85° F. to 115° F.

The continuous stream of $CO_2$ and $O_x$, gas can be prepared by any means. For example, the continuous stream of $O_x$ gas may be prepared in an $O_x$ generation cell that contains a means for generating the $O_x$ gas at a pressure less than about 20 lbs/in$^2$ such as, for example, one or mote of the following: corona discharge, electrical discharge, ultraviolet light, x-ray, radioactive isotope and electron beam. $CO_2$ and smaller concentrations of CO can be added to the $O_x$ generation cell prior to production of $O_x$, or $CO_2$ can be mixed into the $O_x$ gas flow immediately after its formation.

After application of the gaseous blend of $CO_2$ and $O_x$ to the material, the gaseous blend may then be passed through a commercially available catalytic destruct unit to eliminate any residual CO, $O_3$ and $O_1$ before the gas stream is discharged to the atmosphere.

The present invention is also directed to treated food products and other commodities, building structures, transportation containers and/or soil that result from use of the inventive gaseous blend of $CO_2$ and $O_x$ and method.

Additional objects and attendant advantages of the present invention will be set forth in the description and examples that follow, or may be learned from using the gaseous blend or practicing the method of the present invention. These and other objects and advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further objects and attendant advantages, will best be understood by reference to the following detailed description, taken in conjunction with the accompanying drawings.

BRIEF DESCRIPTION OF THE DRAWINGS

In the following description, like parts are designated by like reference numerals throughout the figures.

DESCRIPTION OF THE PREFERRED EMBODIMENTS

Figure 1:
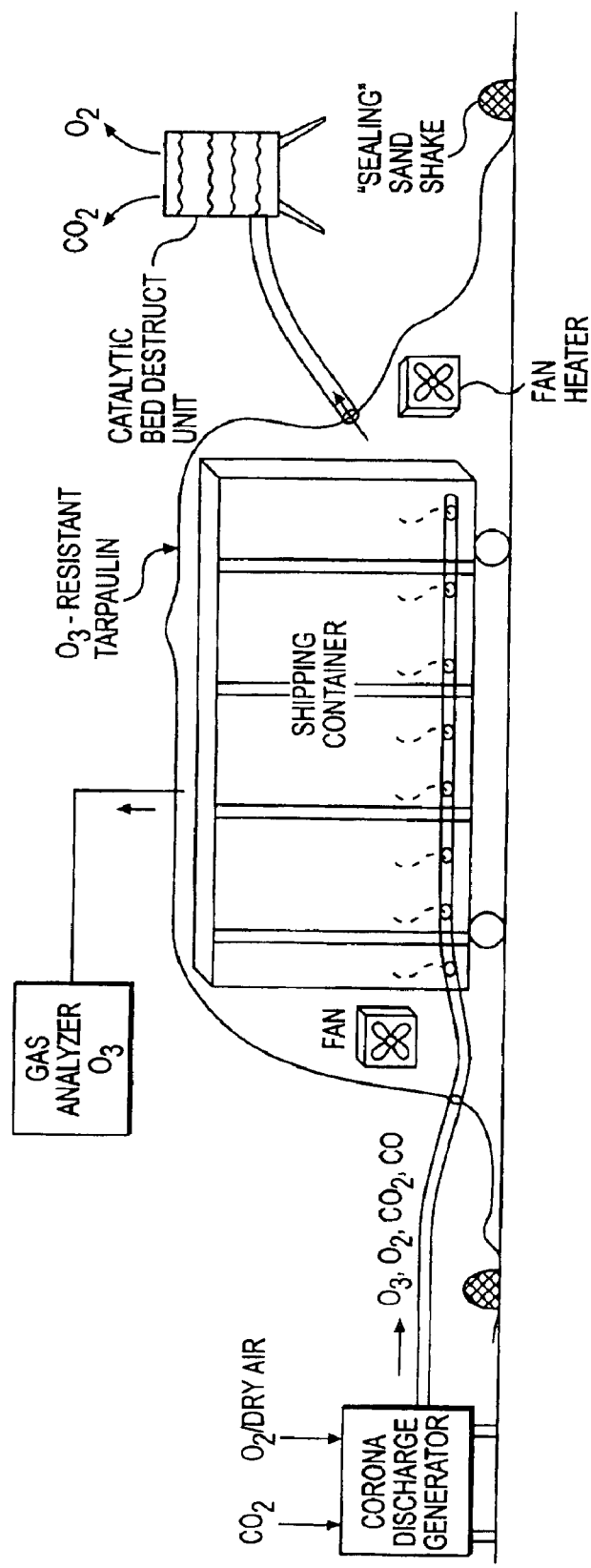
FIG. 1 is a schematic showing an embodiment of a method for using a continuous flow of $CO_2$ and $O_x$ to reduce biological burden in accordance with the method of the present invention.

All patents, patent applications and literatures that may be cited herein are incorporated herein by reference.

The antibacterial potential of $O_3$ has been recognized for many years. $O_3$ is widely used as a disinfectant for sewage treatment and for purification of drinking water. It has, however, failed to gain acceptance as a biological burden reduction treatment. The primary reason for this failure is that the $O_3$ molecule is highly unstable and quickly reverts to $O_2$ if it does not encounter a susceptible substrate with which to react. $O_3$ also has the capacity to react with a broad array of substrates and would be expected to react with packaging materials surrounding the items being treated. This further reduces the number of $O_3$ molecules available to react with and inactivate microbial contaminants.

U.S. Pat. Nos. 5,011,699 and 6,066,348 disclose previous attempts to use $O_3$ as a biological burden reduction treatment that include the reliance upon filling a chamber with $O_3$ and exposing the materials to be treated in static fashion for various periods of time without replenishment of $O_3$. Under these conditions, the concentration of $O_3$ within the chamber would be expected to rapidly decrease to a level below that required for effective biological burden reduction because of the short half life of $O_3$, which is typically less than 20 minutes. A further disadvantage of the static exposure technology is the reliance on simple diffusion to promote permeation of the $O_3$ molecules through packaging materials and into the voids and interstices of the materials being treated. Such methods, therefore, do not achieve adequate permeation of the $O_3$ molecules into the material being treated.

The method of the invention offers significant advances over the prior static biological burden reduction technology in that it provides a continuous flow of $CO_2$ and a continuous flow of $O_x$ throughout the treatment cycle and promotes rapid permeation of $O_x$ through packaging materials and into the voids and interstices of the materials undergoing treatment. The flow of $CO_2$ is between about 90% and 99%, preferably between about 98% and 99%, and the flow of $O_x$ is between about 1% and 10%, preferably between about 1% and 2%. Continuously supplying newly generated $O_x$ molecules to replace those molecules that have spontaneously degraded to inactive $O_2$ and those that have reacted during the process ensures that the concentration of $O_x$ remains essentially the same throughout the process.

The method of the invention also provides significant cost advantages over existing biological burden reduction technology. The most significant savings derive from the fact that the gaseous blend of $CO_2$ and $O_x$ may be generated and applied on site.

Because $O_x$ is not flammable or explosive, facilities need not include damage-limiting construction or explosion-proof equipment. Another advantage of the method of the invention is that scrubbing will be easily accomplished using existing technology. Moreover, $O_3$ is classified by the U.S. Food and Drug Administration as a generally recognized as safe "GRAS" substance.

The gaseous blend of $CO_2$ and $O_x$ and method of the invention has proven successful in the treatment of a wide variety of materials, including food products and other commodities, building structures, transportation containers and soil.

The method of the present invention avoids many of the limitations of previous practices by avoiding the need for water sprays and/or water immersion of the substrate to be treated. Many products such as spices, flour-based products, sugar-based products, cosmetic bases, herbs, and botanicals, all of which are sensitive to high levels of moisture, can be treated using the method of the present invention. The method of the present invention also avoids the need to open conventional commercial packing before treatment, thereby avoiding unnecessary product degradation and loss. The product may be treated in situ utilizing conventional processing. Previous methods have required the product to be agitated, blended, bubbled or re-packaged during or immediately upon completion of the treatment. The extended half life of the $O_x$ radicals allows the active portions of the treatment gas to fully penetrate the substrate and act upon offending organisms. In combination with $CO_2$, the stabilized $O_x$ gas mixture is further enhanced by the increased respiration rates of the offending organism(s) while in the presence of the permeated $O_x$ gases.

According to an embodiment, a gaseous mixture comprised primarily of $CO_2$, as well as smaller concentrations of $O_3$, $O_2$ and carbon monoxide (CO), is used. The gaseous mixture is preferably fed through an ozone generator such as that described above where a gaseous blend is formed consisting of $CO_2$, $O_3$, $O_2$ and CO. This gaseous blend assists in the stabilization of the $O_3$ molecules by dampening the molecular collision of the $O_3$ molecules, which would degrade this triatomic form of oxygen back to its diatomic form, atmospheric oxygen. Several benefits have been observed by generating this gaseous blend. The first benefit is to "tame" the $O_3$ so it has a chance to penetrate into the interstitial spaces of the material being treated. In addition, the $CO_2$ acts as a non-polar solvent to assist in the penetration of the gaseous blend into the material. By reducing the residual oxygen levels equal to or below normal atmospheric levels, oxidative damage to the material is highly reduced. The presence of high levels of $CO_2$ has been shown to enhance the effects of fumigants by promoting increased respiration in insects, thereby allowing the infusion of the fumigant into the insect spiracles and coming into direct contact with the insects' bodily fluids.

As an alternative, the $CO_2$ can be mixed into an $O_3$-rich gas flow immediately after the ozone generator to assist in the formation of the gaseous blend. According to this technique, no CO is formed because no $CO_2$ molecules are cleaved. A disadvantage of this system is the increased amount of oxygen required to produce the $O_3$ in the generator, which subsequently allows the $O_3$ to degrade at an accelerated rate.

This gaseous blend is allowed to flow into, through and out of an impervious tarpaulin or sealed room as a continuous stream for a given period of time. Fans may be utilized to distribute the gaseous blend throughout the enclosed area to effect penetration into the commodity being treated. An outlet for excess gas allows for a constant release of gas through a catalytic bed consisting of, e.g., oxides of manganese, copper and aluminum to destruct any residual $O_3$, $O_1$ and CO. This process has been demonstrated to operate at temperatures between 45° F. and 140° F. Heating units can be incorporated into the fans to assist in bringing the temperature of the material to a desired temperature. The ideal temperature is 85° F. to 115° F.

Produce and the like generally require 1 to 24 hours treatment where other commodities such as grains may require treatment in excess of 48 hours. The concentration as measured directly from the $O_x$ generator can be adjusted to fall within the range of about 10 ppm to about 3,500 ppm, and more preferably about 10 ppm and 1,800 ppm, for food products, and up to about 20,000 ppm for building structures, transportation containers and soil, by using a starting gas mixture of about 90% to 100% $CO_2$, preferably about 98% to 99%, and about 0% to 10%, preferably about 1% to 2% oxygen or air. Although the gas stream flowing through the ozone generator must be extremely dry, no additional moisture is required to humidify the material to be treated.

Agricultural soil may be treated in accordance with the method of the invention, wherein the gaseous blend of $CO_2$ and $O_x$ is continuously fed under a gas impermeable membrane, e.g., a polyethylene film or a fumigation tarpaulin that has proven to be $O_3$ resistant. This process would be typical of a methyl bromide soil fumigation that is routinely performed to control various insects, weed seeds, nematodes and fungal infections. After application, the gaseous blend of $CO_2$ and $O_x$ would be destructed at an exit port.

Infested structures may also be treated in accordance with the method of the invention, wherein the structure is first covered with a gas impermeable membrane and sealed for leaks, and wherein the gaseous blend of $CO_2$ and $O_x$ is then fed continuously and allowed to diffuse into the structure. The gaseous blend is evenly distributed using fans, which could also be used to supply any required additional heat. After application, the gaseous blend of $CO_2$ and $O_x$ would exit a vent and be destructed using a destruct unit.

Figure 2:
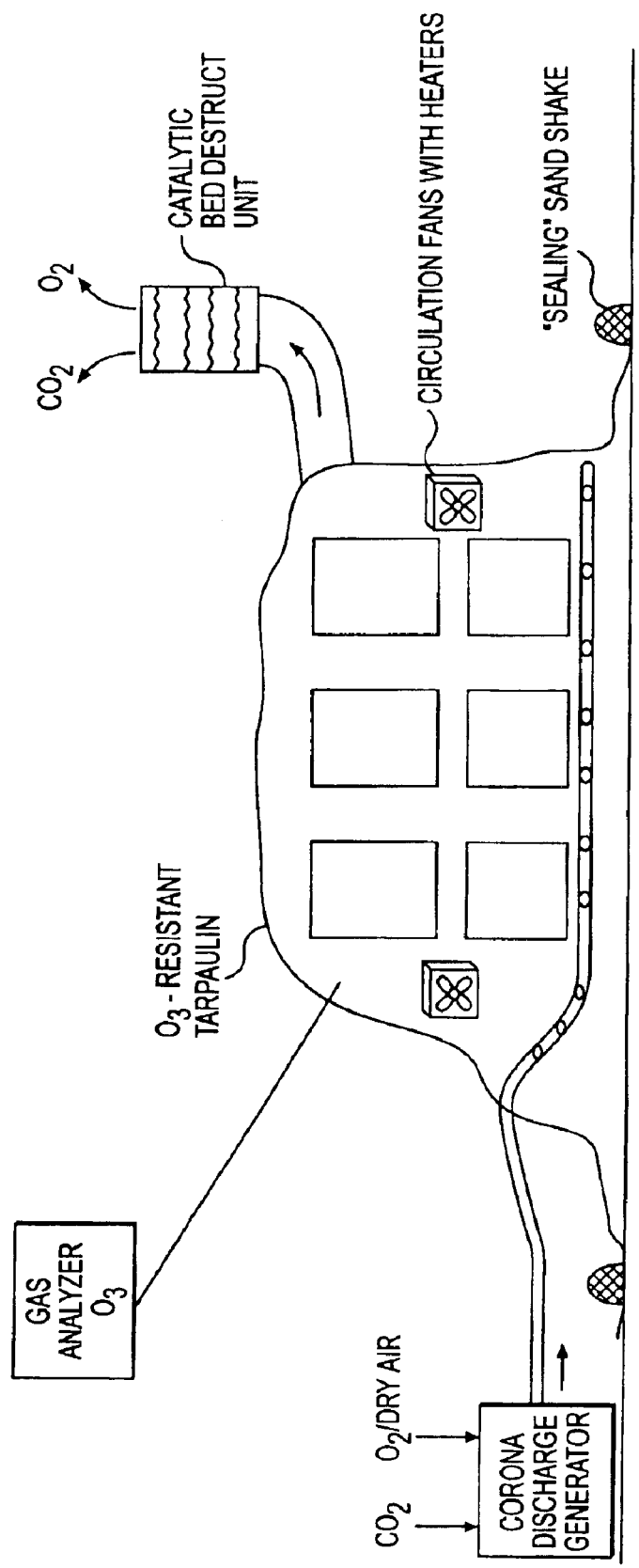
FIG. 2 is a schematic showing another embodiment of a method for using a continuous flow of $CO_2$ and $O_x$ to reduce biological burden in accordance with the method of the present invention.

Referring to FIGS. 1 and 2, the apparatus that may be used to practice the method if the invention includes, e.g., a shipping container 1 (FIG. 1) or storage containers 1' (FIG. 2) that is covered with an $O_3$-resistant tarpaulin 2. The shipping container 1, or storage containers 1', contains material 3 to be treated. The shipping container 1, or storage containers 1', is connected via piping and appropriate control valves to a $O_x$ generator 4 at one end and to a destruct unit 5 at another. A first fan 6 is employed to draw gas from the $O_x$ generator 4 into the shipping container 1 or storage containers 1'. A second fan 6' is employed to draw gas from the shipping container 1 or storage containers 1' to the destruct unit 5. Either the first fan 6 or the second fan 6' may contain a heating means (not shown) to bring the shipping container 1 or the storage containers 1' to a desired temperature. A gas analyzer 7 is employed to determine the concentration of $O_3$ in the shipping container 1 or storage containers 1'.

Referring to FIGS. 1 and 2, according to one embodiment of the invention, material 3 for which biological burden is to be reduced is placed within the shipping container 1 or storage containers 1'. A desired temperature is maintained via heating means (not shown). The process is then initiated by activating the $O_x$ generator 4. A stream of $CO_2$ gas, which may be added to the $O_x$ generator 4 or may be added after generation of $O_x$, and $CO_2$ and $O_x$ gas is then drawn into, through and out of the shipping container 1 or storage containers 1' via the first fan 6 and the second fan 6'. The $O_x$ generator 4 operates continuously during the process.

Exposure to the $CO_2$ and $O_x$ gas mixture may be varied in time from several minutes to several hours, depending on the material being treated. Once the biological burden reduction phase is complete, the $O_x$ generator 4 is inactivated and fresh air is allowed to enter the shipping container 1 or storage containers 1'. All gases may then be passed through destruct unit 5, which eliminates any residual CO, $O_3$ and $O_1$ before the gas stream is discharged to the atmosphere. The treated material 3 is then ready for use following appropriate tests to confirm biological burden reduction.

According to the invention, the material can be treated by applying a continuous stream of $O_x$ and $CO_2$ under atmospheric conditions. This permits the treatment of the material under, e.g., a tarpaulin or in a sealed room, thereby removing the need for a vacuum chamber.

EXAMPLES

The present invention will be further illustrated by the following non-limiting Examples.

Example 1

The gaseous blend of $CO_2$ and $O_x$ and the method of the present invention were used to treat alfalfa pellets for animal feed. The alfalfa pellets were heavily infested with saw-toothed grain beetle adults, grubs and eggs. The alfalfa pellets were placed in a breathable paper sack (sewn) and placed in a treatment room that was equipped with two circulation fans and a heater system. The gaseous blend described below was allowed to flow through the room. The following parameters were used:

| | |
|---|---|
| Gas Mixture: | 99.5% $CO_2$ and 0.5% $O_2$ (mixed prior to $O_3$ generation) |
| Temperature of Room: | 95° F. |
| Relative Humidity: | maintained at less than 20% |
| Final $O_3$ Concentration: | 650 ppm |
| Total time of gas exposure: | 16 hours |
| $O_3$ Generation Technique: | corona discharge |

Results

The alfalfa pellets were observed for sixty days after treatment. No secondary infestation nor any damage to the product was observed.

Example

The gaseous blend of $CO_2$ and $O_x$ and the method of the present invention were used to treat papaya fruits artificially laced with Drosophila fruit flies (adults only). The fruit was placed in normal shipping crates of cardboard construction. The fruit flies were placed in small glass tubes plugged with tissue and located in various locations within the shipping crates. The following parameters were used:

| | |
|---|---|
| Gas Mixture: | 98% $CO_2$ and 2% $O_2$ (mixed prior to $O_3$ generation) |
| Chamber Temperature: | 85° F. |
| Relative Humidity: | maintained at less than 20% |
| Final $O_3$ Concentration: | 1,100 ppm |
| Time of gas exposure: | 60 minutes |
| $O_3$ Generation Technique: | corona discharge |

Results

All flies were killed in the process. No damage to the fruit was observed.

Example

The gaseous blend of $CO_2$ and $O_x$ and the method of the present invention were used to treat fresh strawberries. The strawberries were dipped into a buffered water solution containing a starting titre of 100,000 E. coli bacteria. The strawberries were allowed to air dry and placed into the treatment chamber along with several tubes containing live aphids. The glass tubes were plugged with tissue to retain the insects. A control set of plated strawberries was retained at room temperature for later enumeration. The following parameters were used:

| | |
|---|---|
| Gas Mixture: | 98% $CO_2$, and 2% $O_2$ (mixed prior to $O_3$ generation) |
| Chamber Temperature: | 112° F. |
| Relative Humidity: | maintained below 20% |
| Final $O_3$ Concentration: | 1,600 ppm |
| Time of Gas Exposure: | 60 minutes |
| $O_3$ Generation Technique: | corona discharge |

Results

All insects were killed during the process. The control set of strawberries tested positive for E. coli at the concentration of 6,846 cfu/sq. inch. The treated strawberries tested negative for E. coli and were devoid of any damage to the fruit and the carpels.

The gaseous blend of $CO_2$ and $O_x$ and the method for applying the gaseous blend of $CO_2$ and $O_x$ of the invention are an excellent substitute for commercial sterilants and fumigants in all of their current uses. The gaseous blend and method of the present invention and are also useful for the treatment of many food ingredients on which use of commercial sterilants and fumigants is not permitted, including cocoa beans, grains, and edible gums. Examples of commodities to be treated using the gaseous blend of $CO_2$ and $O_x$ and method of the invention include:

fresh and dried fruits and vegetables, herbs and botanicals, dry pet foods, cotton and other fibers, wood and wood products, grains, livestock feed, transport vehicles, nursery rootstocks, and ornamentals and cut flowers.

Although the invention has been described with some particularity with respect to preferred embodiments thereof, many changes could be made and many alternative embodiments could be derived without departing from the scope of the invention.

What is claimed is:

1. A method for fumigating an enclosed structure to reduce biological burden in said structure, comprising:

releasing a gaseous blend of $O_x$ and $CO_2$ to said enclosed structure, said gaseous blend comprising about 1–10% $O_x$ and about 90–99% $CO_2$; and maintaining said gaseous blend of $O_x$ and $CO_2$ in said enclosed structure for an amount of time sufficient to reduce said biological burden in said structure.

2. The method of claim 1, wherein said gaseous blend comprises about 1–2% $O_x$ and about 98–99% $CO_2$.

3. A method for fumigating a material contained within an enclosed space to reduce biological burden, comprising;

releasing a gaseous blend of $O_x$ and $CO_2$ into said enclosed space, said gaseous blend comprising about 1–10% $O_x$ and about 90–99% $CO_2$ and maintaining said gaseous blend of $O_x$ and $CO_2$ in said enclosed space for an amount of time sufficient to reduce said biological burden on said material.

4. The method of claim 3, wherein said gaseous blend comprises about 1–2% $O_x$ and about 98–99% $CO_2$.

5. A method for fumigating soil in a field to reduce biological burden, comprising:
   placing a gas impermeable membrane over said soil to provide an enclosed space above said soil; releasing a gaseous blend of $O_x$ and $CO_2$ into said enclosed space, said gaseous blend comprising about 1–10% $O_x$ and about 90–99% $CO_2$ and
   maintaining said gaseous blend of $O_x$ and $CO_2$ in said enclosed space for an amount of time sufficient to reduce said biological burden in said soil.

6. The method of claim 5, wherein said gaseous blend comprises about 1–2% $O_x$ and about 98–99% $CO_2$.

7. A fumigant system comprising a gaseous blend of $O_x$ and $CO_2$, said gaseous blend comprising about 1–10% $O_x$ and about 90–99% $CO_2$.

8. The system of claim 7, wherein said gaseous blend comprises about 1–2% $O_x$ and about 98–99% $CO_2$.

9. A method for fumigating a material, comprising:
   placing said material in an enclosed space; and
   applying a continuous stream of $O_x$ and $CO_2$ through said enclosed space, wherein said $O_x$ includes oxygen and its radicals and wherein x is an integer from 1 to 3.

10. The method of claim 9, wherein a temperature within said enclosed space is maintained at about 45° F. to about 140° F.

11. The method of claim 10, wherein a temperature within said enclosed space is maintained at about 85° F. to about 115° F.

12. The method of claim 9, wherein said $O_x$ is generated within an $O_x$ generation cell and wherein said $CO_2$ is introduced into said $O_x$ generation cell prior to said $O_x$ generation.

13. The method of claim 9, wherein said $O_x$ is generated within an $O_x$ generation cell and wherein said $CO_2$ is introduced after generation of said $O_x$.

14. The method of claim 12, wherein said $CO_2$ and said $O_x$ are withdrawn from said $O_x$ generation cell into said enclosed space; and
   wherein said $CO_2$ and said $O_x$ are withdrawn from said enclosed space.

* * * * *